(12) United States Patent
Merkel

(10) Patent No.: US 11,174,222 B2
(45) Date of Patent: *Nov. 16, 2021

(54) MULTISTEP PROCESS FOR THE PREPARATION OF DIISOCYANATES

(71) Applicant: Covestro Deutschland AG, Leverkusen (DE)

(72) Inventor: Michael Merkel, Düsseldorf (DE)

(73) Assignee: Covestro Deutschland AG, Leverkusen (DE)

( * ) Notice: Subject to any disclaimer, the term of this patent is extended or adjusted under 35 U.S.C. 154(b) by 42 days.

This patent is subject to a terminal disclaimer.

(21) Appl. No.: 16/645,880

(22) PCT Filed: Sep. 12, 2018

(86) PCT No.: PCT/EP2018/074636
§ 371 (c)(1),
(2) Date: Mar. 10, 2020

(87) PCT Pub. No.: WO2019/063295
PCT Pub. Date: Apr. 4, 2019

(65) Prior Publication Data
US 2020/0277253 A1    Sep. 3, 2020

(30) Foreign Application Priority Data

Sep. 26, 2017 (EP) ..................... 17193251

(51) Int. Cl.
C07C 263/00 (2006.01)
C07C 263/04 (2006.01)

(52) U.S. Cl.
CPC .................. C07C 263/04 (2013.01)

(58) Field of Classification Search
CPC .................................................. C07C 263/04
See application file for complete search history.

(56) References Cited

U.S. PATENT DOCUMENTS

| | | | |
|---|---|---|---|
| 3,992,430 | A | 11/1976 | Backsai |
| 5,386,053 | A | 1/1995 | Otterbach et al. |
| 7,339,074 | B2 | 3/2008 | Kohlstruk et al. |
| 2010/0029981 | A1 | 2/2010 | Shinohata et al. |
| 2014/0194650 | A1* | 7/2014 | Shinohata ............. C07C 269/04 560/345 |

FOREIGN PATENT DOCUMENTS

| | | |
|---|---|---|
| EP | 0320235 A2 | 6/1989 |
| EP | 2147909 A1 | 1/2010 |
| EP | 2679575 A1 | 1/2014 |

OTHER PUBLICATIONS

International :Search Report, PCT/EP2018/074636, dated Nov. 27, 2018, Authorized officer: J. Matés Valdivielso.

* cited by examiner

Primary Examiner — Sikarl A Witherspoon
(74) Attorney, Agent, or Firm — John E. Mrozinski, Jr.

(57) ABSTRACT

Provided is a process for preparing an organic diisocyanate of the formula: OCN—R—NCO (1), wherein R represents a bivalent hydrocarbon radical containing 3 to 20 carbon atoms, the carbon atoms being arranged in a way that the two nitrogen atoms are separated from each other by at least 3 carbon atoms, the process comprising, Step (I) preparing a diurethane of the formula

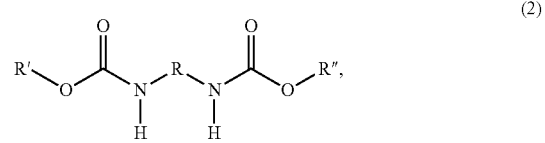

(2)

wherein R is the same as in formula (1), R' and R" independently represent organic radicals selected from the group consisting of 4 to 36 carbon atoms, 4 to 74 hydrogen atoms, 0 to 12 oxygen atoms that have the oxidation state –2, and 0 to 1 halogen atoms from a diarylurethane of the formula,

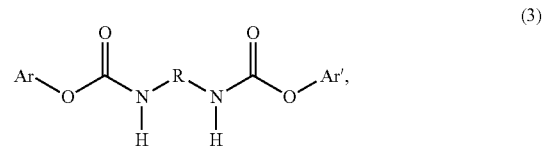

(3)

wherein R is the same as in formula (1), Ar and Ar' independently represent a substituted or unsubstituted aryl or heteroaryl radical selected from the group containing a total of 4 to 20 carbon atoms by transesterification, Step (II) subjecting the diurethane of the formula (2) to a cleavage reaction to form the hydroxy compounds R'—OH and R"—OH and the organic diisocyanate of the formula (1), Step (III) separating the diisocyanate of the formula (1) from the hydroxy compounds R'—OH and R"—OH by distillation, wherein the hydroxy compounds R'—OH and R"—OH have higher standard boiling points than the standard boiling point of the diisocyanate OCN—R—NCO and the sum of the molecular weights of the radicals Ar and Ar' is lower than the sum of the molecular weights of the radicals R' and R".

14 Claims, No Drawings

MULTISTEP PROCESS FOR THE PREPARATION OF DIISOCYANATES

CROSS REFERENCE TO RELATED APPLICATIONS

This application is a national stage application under 35 U.S.C. § 371 of PCT/EP2018/074636, filed Sep. 12, 2018, which claims benefit of European Application No. 17193251.0, filed Sep. 26, 2017, both of which are incorporated herein by reference in their entirety.

FIELD OF THE INVENTION

The present invention relates to a multistep process for the preparation of organic diisocyanates by cleavage of diurethanes that have been derived from diarylurethanes of lower molecular weight into the corresponding diisocyanates and hydroxy compounds and separating these cleavage products by distillation.

BACKGROUND OF THE INVENTION

The industrial processes for the preparation of organic diisocyanates, be it aromatic, aliphatic or cycloaliphatic disocyanates, are commonly based on phosgenation of the corresponding diamines. There have been numerous efforts to avoid use of phosgene in the synthesis of the organic diisocyanates not only due to the toxicity of phosgene, but also in order to avoid producing large quantities of hydrogen chloride as a byproduct.

The most common phosgene free route for the production of isocyanates is the thermal cleavage of the corresponding urethanes that yields alcohols and isocyanates. It has been described numerous times. For example EP 1 512 682 A1 describes a multi stage process for the production of cycloaliphatic diisocyanates. In the first stage, a diurethane is formed from the reaction of diamine, carbonic acid derivative, and a hydroxy compound. The hydroxy compound is an alcohol having a boiling point below 190° C. at normal pressure and preferably it is 1-butanol. After purification of the obtained diurethane, it is thermally cleaved in a second stage to obtain the cycloaliphatic diisocyanate and a hydroxy compound.

In order to suppress recombination of hydroxy compound and isocyanate, a highly quantitative separation of the thermal cleavage products is desirable. To achieve this, U.S. Pat. No. 5,386,053 describes the use of hydroxy compounds having boiling points that are sufficiently far from the boiling point of the diisocyanate. Thus, preference is given to aliphatic hydroxy compounds, and in particular to n-butanol and/or isobutanol which have boiling points far below the boiling points of industrially relevant diisocyanates. However, when using such low boiling hydroxy compounds, the hydroxy compounds will be obtained as a distillate and the isocyanate will be the bottom product when the crude product is refined in a distillation step. Therefore, it will still contain high boiling impurities, like carbamic acid alkyl esters (urethanes). Furthermore, the use of catalysts for the thermolytic cleavage reaction becomes difficult in this setup because catalyst will be entrained in the isocyanate where it may facilitate reactions of the iscocyanate groups and reduce shelf life of the product. If this bottom product is distilled again in a downstream process step after removal of the hydroxy compound, the isocyanate is in the distillate fraction. Nevertheless it will be difficult to achieve high purity, because the high boiling impurities can cleave and release the low boiling hydroxy compounds which again would be part of the distillate and recombine with the diisocyanate.

Recently, in EP 2 679 575 A1, a process has been described that comprises the step of subjecting an N-substituted carbamic acid ester to a thermal cleavage reaction. It is described that aromatic hydroxy compounds are preferred hydroxy compounds for the formation of the carbamic acid ester which results in the formation of carbamic acid-O-aryl esters that undergo thermal cleavage more easily compared to carbamic acid-O-alkyl esters. The aromatic hydroxy compounds mentioned in the document include for example t-octylphenol, 2,4-di-t-amylphenol or p-cumylphenol which have boiling points higher than the boiling points of industrially relevant diisocyanates like hexamethylene diisocyanate, pentamethylene diisocyanate, or isophorone diisocyanate. This combination allows thermal cleavage and subsequent distillation with the isocyanate being the distillate rather than the bottom product so that efficient separation of isocyanate and hydroxy compound is possible.

The disadvantage of this process is related to the high molecular weights of the aromatic hydroxy compounds having higher boiling points as the diisocyanates. In the formation of the O-arylurethanes, it is desirable to use high stoichiometric excess of the hydroxy compound based on the amount of amino groups of the organic primary amine used. A preferred range of 2:1 to 50:1 is mentioned. This leads to very high mass flows of the hydroxy compound which is linked to high energy consumptions for conveying, heating, evaporating, condensing and cooling the hydroxy compound in the course of the process. Furthermore, the substituted aromatic hydroxy compounds are of limited stability under the reaction conditions, leading to losses and additional efforts for treating, disposing or recycling the decomposition products.

EP 0 320 235 A2 describes the formation of aliphatic O-arylurethanes that can be used as precursors for isocyanates. Preference is given to mono hydroxy compounds and particularly to phenols having low boiling points as the aromatic hydroxy compounds in order to achieve easy separation. However, this preference for phenol comes along with the above mentioned problems of isocyanate purification and restrictions in the use of catalysts. The problem of high processing cost caused by the high mass flows when using higher molecular weight aromatic hydroxy compounds is not mentioned.

EP 2 679 575 A1 and EP2088137 B1 both describe a transesterification step that allows conversion of dialkylurethanes or diaralkylurethanes into diarylurethanes. The main purpose of the transesterification in these documents is the formation of diarylurethanes which allow thermal cleavage reaction to the diisocyanate at milder conditions and with less byproducts than the dialkyl- or diaralkylurethanes. A preference for higher boiling alcohols that allow better purification of the isocyanate is not described.

DETAILED DESCRIPTION OF THE INVENTION

Therefore, it was an object of the present invention to provide a phosgene free and efficient multi-step process for preparing organic diisocyanates which allows fast separation of the diisocyanate from the hydroxy compound in the form of a distillate.

This object was solved by a process for preparing an organic diisocyanate of the general formula (1)

$$OCN-R-NCO \qquad (1)$$

wherein
R represents a bivalent hydrocarbon radical containing 3 to 20 carbon atoms and the carbon atoms being arranged in a way that the two nitrogen atoms are separated from each other by at least 3 carbon atoms, comprising the following steps:
(I) preparing a diurethane of the general formula (2),

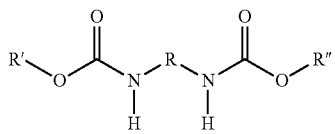
(2)

wherein
R is the same as in general formula (1),
R' and R" independently from each other represent organic radicals selected from the group consisting of 4 to 36 carbon atoms, 4 to 74 hydrogen atoms, 0 to 12 oxygen atoms that have the oxidation state −2, and 0 to 1 halogen atoms
from a diarylurethane of the general formula (3),

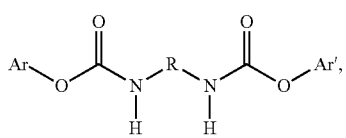
(3)

wherein
R is the same as in general formula (1),
Ar and Ar' independently from each other represent a substituted or unsubstituted aryl or heteroaryl radical selected from the group containing a total of 4 to 20 carbon atoms
by transesterification reaction,
(II) subjecting the diurethane of the general formula (2) to a cleavage reaction to form the hydroxy compounds R'—OH and R"—OH and the organic diisocyanate of the general formula (1),
(III) separating the diisocyanate of the general formula (1) from the hydroxy compounds R'—OH and R"—OH by distillation,
characterized in that
the hydroxy compounds R'—OH and R"—OH have higher standard boiling points than the standard boiling point of the diisocyanate OCN—R—NCO and
the sum of the molecular weights of the radicals Ar and Ar' is lower than the sum of the molecular weights of the radicals R' and R".

The process of the present invention allows production of diisocyanates of the general formula (1) in high purity. The diisocyanates are diisocyanates in which the nitrogen atoms of the NCO groups are separated from each other by at least 3 carbon atoms, preferably at least 4 carbon atoms. This reduces the risk of intramolecular ring formation in the underlying reaction steps. Thus, the term "separated from each other by at least 3 carbon atoms" is to be understood in a way that the 2 nitrogen atoms are not attached to the same carbon atom or directly adjacent carbon atoms but rather to 2 different carbon atoms that are separated from each other by at least one further carbon atom. The bonds between the carbon atoms may be single bonds and/or bonds of a higher order.

A preferred embodiment of the invention is the above mentioned process for preparing an organic diisocyanate of the general formula (1)

OCN—R—NCO (1), wherein
R represents a bivalent hydrocarbon radical which can be derived from 2,4-toluene diisocyanate, 2,6-toluene diisocyanate, hexamethylene diisocyanate, pentamethylene diisocyanate or isophoronediisocyanate by removing the two isocyanate groups,
comprising the following steps:
(I) preparing a diurethane of the general formula (2)

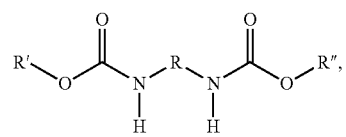
(2)

wherein
R is the same as in general formula (1),
R' represents a hydrocarbon-substituted or unsubstituted aryl radical selected from the group consisting of 6 to 20 carbon atoms and 5 to 33 hydrogen atoms that is bound to the urethane group of the diurethane of the general formula (2) via a carbon atom that is part of an aromatic ring system and
R" is the same as R',
from a diarylurethane of the general formula (3),

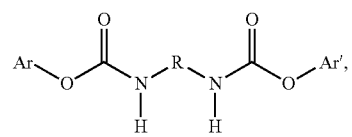
(3)

wherein
R is the same as in general formula (1) and
Ar represents a hydrocarbon-substituted or unsubstituted aryl radical selected from the group containing a total of 6 to 15 carbon atoms and having a lower molecular weight than the radical R' and
Ar' is the same as Ar
by transesterification reaction
(II) subjecting the diurethane of the general formula (2) to a cleavage reaction to form the aromatic hydroxy compounds R'—OH and R"—OH and the organic diisocyanate of the general formula (1),
(III) separating the diisocyanate of the general formula (1) from the aromatic hydroxy compounds R'—OH and R"—OH by distillation,
characterized in that
the aromatic hydroxy compounds R'—OH and R"—OH have a higher standard boiling point than the standard boiling point of the diisocyanate OCN—R—NCO, and
the aromatic hydroxy compound Ar—OH, formally derived from Ar by adding a hydroxy group, has a lower standard boiling point than the standard boiling point of the diisocyanate OCN—R—NCO.

Another preferred embodiment of the invention is the above mentioned process for preparing an organic diisocyanate of the general formula (1),

wherein the organic diisocyanate is hexamethylene diisocyanate, comprising the following steps:
(I) preparing N,N'-hexanediyl-di(carbamic acid(4-cumylphenyl)ester) as diurethane of the general formula (2)

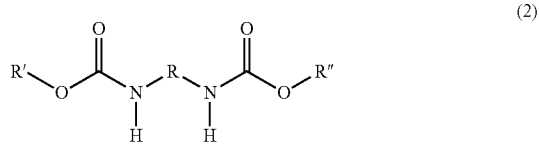

by a transesterification reaction of 1,6-hexamethylene-O,O'-diphenylurethane as diarylurethane of the general formula (3)

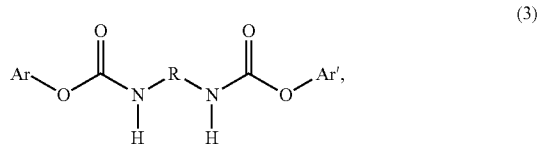

with p-cumylphenol.
(II) subjecting N,N'-hexanediyl-di(carbamic acid(4-cumylphenyl)ester) as diurethane of the general formula (2) to a thermal cleavage reaction to form p-cumylphenol and hexamethylene diisocyanate (HDI)
(III) separating the HDI from the p-cumylphenol by distillation.

In a preferred embodiment of the invention, the diarylurethanes of the general formula (3) are prepared from organic diamines, carbonic acid derivatives and aromatic hydroxy compounds. For the preparation of diarylurethanes, various routes have been described (see for example EP 2 679 575 A1 (examples 5, 6 or 21) or EP 0 320 235 A2 (entire document)). These routes can be adapted by the skilled artisan for the formation of diarylurethanes of the general formula (3). It is preferred to carry out the reaction using a distillation column. The advantages of such an embodiment over other possible reactor types are a pre-purification of the produced diarylurethanes and at least a partial removal of low boiling byproducts that can be formed during the reaction and/or excess starting materials. The diarylurethane can be obtained in good yield at a discharge port being located at the bottom of the column. The distillate is preferably cooled in a way that allows partial condensation of the distillate. The liquids are then recycled to the feed of the column in order to optimize the use of starting materials and reduce material consumption, while a gaseous stream containing low boiling byproducts is unloaded from the process. These byproducts can later on be recovered from the gas stream, for example by condensation or absorption, for further commercial use, incineration or disposal.

Suitable starting materials for formation of the diarylurethanes of the general formula (3) are organic diamines, carbonic acid derivatives and aromatic hydroxy compounds. The reaction can be carried out as a one stage synthesis or in a multi-stage process where parts of the starting material are pre-reacted at mild conditions before conversion to the diarylurethanes is performed. During the abovementioned pre-reaction, the carbonic acid derivative is present and the organic diamine and/or the aromatic hydroxy compound. The pre-reaction preferably takes place at temperatures below 180° C., more preferably below 150° C. In another preferred embodiment, released low boiling byproducts can be removed from the reaction via the gaseous phase. Suitable reactors for the pre-reaction step are for example stirred vessels, but also other reactor types can be utilized. Such a pre-reaction is particularly useful if urea is used as the carbonic acid derivative. In that case, the organic diamine is converted into the corresponding diurea compound under release of ammonia. Removing ammonia from the reaction system helps to drive reaction to completion.

The products of the pre-reaction stage, or, in case of a one stage synthesis the organic diamine and the carbonic acid derivative, are then converted with at least one aromatic hydroxy compound, preferably in presence of carbonic acid derivative, to the diarylurethane of the general formula (3) at a reaction temperature between 180 and 280° C., preferably between 200 and 260° C. and most preferably between 200 and 240° C.

The gross reaction scheme for the formation of the diarylurethanes of the general formula (3) is as follows:

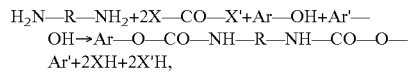

wherein R, Ar and Ar' are as defined in formula (1) and formula (3), respectively, and X and X' are independently of one another selected from NH$_2$, O-Alkyl, O-Aryl and Cl with the proviso that X' is not Cl if X is Cl.

Preferred diamines for formation of the diarylurethanes of the general formula (3) wherein R represents a bivalent hydrocarbon radical containing 3 to 20 carbon atoms and the carbon atoms being arranged in a way that the two nitrogen atoms are separated from each other by at least 3 carbon atoms, are 2,4- and/or 2,6-toluylendiamine (TDA), 2,2'-, 2,4'- and/or 4,4'-diaminodiphenylmethane (MDA), 1,5-naphthalenediamine (NDA), 1,3- and/or 1,4-diaminobenzene, m-xylylenediamine, p-xylylendiamine, 1,4-butanediamine, neopentanediamine, 1,5-pentanediamine (PDA), 1,5-diamino-2-methylpentane, 2-butyl-2-ethyl-1,5-pentanediamine, 1,6-hexanediamine (HDA), 2,5-diamino-2,5-dimethylhexane, 1-amino-3,3,5-trimethyl-5-aminomethyl-cyclohexane (IPDA), 1,4-cyclohexanediamine, 2,4- and/or 2,6-hexahydrotoluenediamine (H6-TDA), isomers of hexahydroxylylendiamine (H6-XDI), isomers of bis-(aminomethyl)norbornane, or mixtures of the aforementioned. Particularly preferred diamines are TDA, PDA, HDA and IPDA. The most preferred diamine is HDA, because of its high industrial relevance, its high thermal stability, the moderate reactivity of the corresponding diisocyanate (hexamethylene diisocyanate (HDI)) and the favorable boiling point of HDI that allows an economically favorable selection of hydroxy compounds that meet the requirements of the present invention.

The carbonic acid derivatives used for the formation of the diarylurethanes of the general formula (3) can be urea, urethane, carbamoylchloride, carbamate ester, diarylcarbamate or dialkylcarbamate. Preferably, the carbonic acid derivative is urea, diarylcarbamate or dialkylcarbamate. Most preferably the carbonyl derivative is urea because it is easily available at low cost and it will release NH$_3$ in the course of the reaction which can easily be removed from the reaction mixture in order to shift the equilibrium towards the desired diurethanes.

The aromatic hydroxy compounds used for the formation of the diarylurethanes of the general formula (3) are such hydroxy compounds wherein the OH group is bonded to a carbon atom that is part of an aromatic ring. Such aromatic hydroxy compounds are beneficial because they are relatively good solvents for urea or other compounds bearing urea groups and they are easily condensed even under vacuum conditions. Preferably, the aromatic hydroxy compound is selected from the group consisting of phenol, o-cresol, m-cresol, p-cresol, 2,6-xylenol, 2,5-xylenol, 2,4-xylenol, 2,3-xylenol, 3,4-xylenol, 3,5-xylenol, mesitol, o-ethylphenol, m-ethylphenol, p-ethylphenol, isomers of propylphenol, isomers of butylphenol. These have relatively small molecular weights for aromatic hydroxy compounds and therefore lower mass flows are required to perform the necessary reactions. If only one hydroxy compound is selected, the groups Ar and Ar' in the diurethane of the general formula (2) will be the same. However, it is also preferred to use a combination of 2 or more of these aromatic hydroxy compounds for the formation of the diarylurethane, e.g. in order obtain a mixture of hydroxy compounds with a lower melting point than the single hydroxy compounds. Most preferably, the hydroxy compound is phenol as it is stable under reaction conditions and commercially available at low cost. A process for the preparation of 1,6-hexamethylene-O,O'-diphenylurethane is also described in EP 0 320 235 A2 (see e.g. example 1) and such process can be adapted for the formation of the diarylurethane compound of the general formula (3).

The conversion of the diarylurethane compound of the general formula (3) into the diurethane of the general formula (2) is done by subjecting the diarylurethane of the general formula (3) to a transesterification reaction with the hydroxy compounds R'—OH and R"—OH, thereby replacing the Ar—O and/or Ar'—O groups with R'—O and/or R"—O groups and forming the diurethane of the general formula (2) and the aromatic hydroxy compounds Ar—OH and Ar'—OH. In the following, this reaction is simply referred to as transesterification.

In a preferred embodiment of the invention, the diarylurethane of the general formula (3) is selected in a way that the corresponding aromatic hydroxy compounds Ar—OH and Ar'—OH have a standard boiling point lower than the diisocyanate OCN—R—NCO. This allows operating the process at conditions that minimize losses of the diisocyanate.

The transesterification can in principle be carried out as described, for example, in [0054]-[0061] of EP 2 088 137 B1 for the transesterification of dialkylurethanes with aromatic hydroxy compounds into diarylurethanes. This process is also applicable when diarylurethanes are used as starting material for the transesterification. Suitable starting materials in the transesterification are the diarylurethane and the hydroxyl compounds R'—OH and optionally R"—OH. In a preferred embodiment of the invention, the hydroxy compounds R'—OH and R"—OH in the transesterification are used in an amount that the combined number of OH groups from R'—OH and R"—OH is higher than that of the urethane groups in the transesterification reaction mixture. In a more preferred embodiment, the aromatic hydroxy compounds are used in an amount that the number of OH groups is between 2 and 50 times as high as the number of urethane groups. Most preferably, the number of OH groups between 2 and 20 times as high as the amount of urethane groups.

In another preferred embodiment, the transesterification is carried out in a continuous process. Optionally the diarylurethane can be introduced into the transesterification reactor together with a solvent. Preferably the solvent is Ar—OH, Ar'—OH or a mixture of both so that a complete removal of the excess aromatic hydroxy compounds in the formation of the diarylurethane of the general formula (3) is not required.

During the transesterification, Ar—OH and Ar'—OH are formed. In a preferred embodiment of the invention, the standard boiling point of these aromatic hydroxyl compounds is lower, preferably more than 5 K lower, more preferably between 20 K and 135 K lower and most preferably between 50K and 100 K than that of the diisocyanate OCN—R—NCO. This can be achieved by using a diarylurethane of the general formula (3) wherein the Ar and Ar' radicals as defined above correspond to aromatic hydroxy compounds Ar—OH and Ar'—OH that have the right lower standard boiling points relative to the diisocyanate OCN—R—NCO (The Ar—OH and Ar'—OH can formally be obtained by adding OH to the radicals Ar and Ar', respectively). The advantage of this embodiment is that it is easy to remove Ar—OH via the vapor phase with only minimal losses of OCN—R—NCO which may be formed in a side reaction during transesterification. At the same time, in case these aromatic hydroxy compounds are also present as solvents, they are also removed from the reaction system at this stage. By doing so, the equilibrium reaction is pushed to completion resulting in a high yield of the desired R'—O—CO—NH—R—NH—CO—O—R".

The hydroxy compounds R'—OH and R"—OH used for the transesterification can be any hydroxy compounds that have standard boiling points higher, preferably between 5 K and 150 K, more preferably between 10 K and 120 K and most preferably between 20 K and 100 K higher than the standard boiling point of the organic diisocyanate OCN—R—NCO and in which the hydroxy group is attached to a carbon atom of an organic radical selected from the group consisting of 4 to 36 carbon atoms, 4 to 74 hydrogen atoms, 0 to 12 oxygen atoms that have the oxidation state −2, and 0 to 1 halogen atoms. This allows an efficient separation of hydroxy compound and diisocyanate via distillation in the later steps of this process. The standard boiling point of a compound is defined according to the IUPAC definition as the temperature at which boiling of the compound occurs under a pressure of 1 bar.

In another preferred embodiment of the invention, the hydroxy compounds R'—OH and R"—OH having standard boiling points higher than that of the organic diisocyanate OCN—R—NCO are one or more aromatic hydroxy compounds, preferably 1-naphthol, 2-naphthol, tert-octylphenol, 2,4-di-tert-amylphenol or p-cumylphenol. The most preferred aromatic hydroxy compound for the is p-cumylphenol as it contains only one hydroxy-group and has a boiling point high enough for a good separation from the diisocyanate after the cleavage and a relatively low melting point which is beneficial for handling the hydroxy compound and starting the process. The same compounds R'—OH and R"—OH are also preferably used as hydroxyl compounds if transesterification is used to convert the diarylurethan of the general formula (3) into the diurethane of the general formula (2).

In another, equally preferred embodiment, the hydroxy compounds for the transesterification having a standard boiling point higher than that of the organic diisocyanate OCN—R—NCO are one or more fatty alcohols, preferably lauryl, stearyl, cetyl or oleyl alcohol. The most preferred fatty alcohols are stearyl alcohol and cetyl alcohol. Such aliphatic alcohols lead to a faster transesterification due to the higher stability of the urethanes containing aliphatic residues R' and R". On the other hand, aromatic alcohols lead to a faster cleavage in the step (I) of the present invention.

If used in sufficient excess, particularly in an amount that allows to essentially prevent reaction of both hydroxy groups, even bisphenol A can be used as the hydroxy compound for the transesterification.

It is not required to use catalysts in the transesterification reaction, but in order to facilitate the reaction, for example (Lewis-)acidic catalysts can be used. It is preferred to use catalysts that are non-volatile or that at least have standard boiling points as high as or higher than standard boiling points of the diisocyanate OCN—R—NCO. That way, they can be separated from the diisocyanate in steps (I) and/or (II), preferably together with the hydroxy compounds Ar—OH and Ar'—OH.

The cleavage of the diurethane of the formula (2) in step (I) and the distillative separation of the obtained diisocyanate OCN—R—NCO from the generated hydroxy compounds can optionally be carried out simultaneously, if the cleavage reaction is carried out in a suitable reactor as for example a column type reactor. However, it is preferred to separate the steps (I) and (II) so that cleavage takes place first and then the cleavage products are subjected to the separation step (II). Both steps can be carried out in a similar manner as described in sections [0371]-[0404] of EP 2 679 575 A1. In a preferred embodiment, the cleavage is a thermolytic cleavage and it is carried out in a thin film evaporator with the aromatic hydroxy compound and the diisocyanate leaving the evaporator as the gaseous phase and at least part of the liquid effluent which will still contain unreacted carbamic acid ester being recycled to the thin film evaporator and again being exposed to thermolytic cleavage conditions. Optionally, a catalyst can be used in the thermolytic cleavage reaction. Suitable catalysts are the same as described for the transesterification reaction above. If catalysts are used in the transesterification reaction, they may be carried over to the cleavage reactor without the need of separating them from the diurethane. To avoid accumulation of high boiling components in the reaction system, at least a part of the liquid effluent of the cleavage reactor can be purged from the system. It is preferred to carry out the cleavage of the diurethanes in a continuous reaction.

Isocyanate and hydroxy compound formed in (I) are preferably transferred to the separation step (II) via the gaseous phase. That way, energy losses during condensation and re-evaporation are avoided. In another preferred embodiment the separation is performed by means of distillation in a packed column. Upon distillation, the diisocyanate is obtained as the distillate and the bottom product contains mainly the hydroxy compounds Ar—OH and, if applicable, Ar'—OH. In a preferred embodiment of the invention, the hydroxy compounds are reused in the transesterification reaction that converts the diarylurethane of the general formula (3) into the diurethane of the general formula (2), optionally after being subjected to a purification step. Preferably, such a purification step is a washing step or more preferably it is a distillation step. If a catalyst with a similar boiling point as Ar'—OH was used in the transesterification, it can be recycled to the transesterification together with the hydroxy compound obtained here. A similar boiling point with regard to the present invention is preferably a boiling point that is between the boiling point of the organic diisocyanate and the diarylurethane compounds present in the thermal cleavage reactor.

The invention particularly relates to the following embodiments:

According to a first embodiment, the present invention relates to a process for preparing an organic diisocyanate of the general formula (1)

OCN—R—NCO (1)

wherein
R represents a bivalent hydrocarbon radical containing 3 to 20 carbon atoms and the carbon atoms being arranged in a way that the two nitrogen atoms are separated from each other by at least 3 carbon atoms,
comprising the following steps:
(I) preparing a diurethane of the general formula (2),

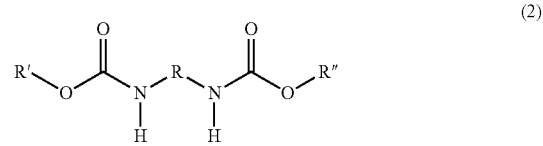

wherein
R is the same as in general formula (1),
R' and R" independently from each other represent organic radicals selected from the group consisting of 4 to 36 carbon atoms, 4 to 74 hydrogen atoms, 0 to 12 oxygen atoms that have the oxidation state −2, and 0 to 1 halogen atoms
from a diarylurethane of the general formula (3),

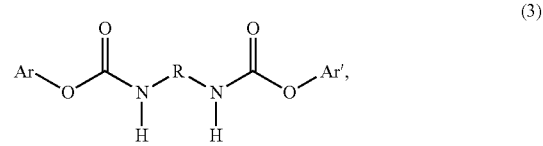

wherein
R is the same as in general formula (1),
Ar and Ar' independently from each other represent a substituted or unsubstituted aryl or heteroaryl radical selected from the group containing a total of 4 to 20 carbon atoms
by transesterification reaction,
(II) subjecting the diurethane of the general formula (2) to a cleavage reaction to form the hydroxy compounds R'—OH and R"—OH and the organic diisocyanate of the general formula (1),
(III) separating the diisocyanate of the general formula (1) from the hydroxy compounds R'—OH and R"—OH by distillation,
characterized in that
the hydroxy compounds R'—OH and R"—OH have higher standard boiling points than the standard boiling point of the diisocyanate OCN—R—NCO, and
the sum of the molecular weights of the radicals Ar and Ar' is lower than the sum of the molecular weights of the radicals R' and R".

According to a second embodiment, the present invention relates to a process according to embodiment 1, wherein the diarylurethanes of the formula (3) have been prepared from organic diamines, carbonic acid derivatives and aromatic hydroxy compounds.

According to a third embodiment, the present invention relates to a process according to embodiment 2, wherein the organic diamine is selected from the group of 2,4- and/or 2,6-toluylendiamine (TDA), 2,2'-, 2,4'- and/or 4,4'-diaminodiphenylmethane (MDA), 1,5-naphthalenediamine (NDA), 1,3- and/or 1,4-diaminobenzene, m-xylylenediamine, p-xylylenediamine, 1,4-butanediamine, neopentanediamine, 1,5-pentanediamine (PDA), 1,5-diamino-2-methylpentane, 2-butyl-2-ethyl-1,5-pentanediamine, 1,6-hexanediamine (HDA), 2,5-diamino-2,5-dimethylhexane, 1-amino-3,3,5-trimethyl-5-aminomethyl-cyclohexane (IPDA), 1,4-cyclohexanediamine, 2,4- and/or 2,6-hexahydrotoluenediamine (H6-TDA), isomers of hexahydroxylylendiamine (H6-XDI), isomers of bis-(aminomethyl)norbornane, or mixtures of the aforementioned According to a fourth embodiment, the present invention relates to a process according to embodiment 2 or 3, wherein the carbonic acid derivative is urea, diarylcarbamate or dialkylcarbonate.

According to a fifth embodiment, the present invention relates to a process according to any of the embodiments 2 to 4, wherein the aromatic hydroxy compound is selected from the group consisting of phenol, o-cresol, m-cresol, p-cresol, 2,6-xylenol, 2,5-xylenol, 2,4-xylenol, 2,3-xylenol, 3,4-xylenol, 3,5-xylenol, mesitol, o-ethylphenol, m-ethylphenol, p-ethylphenol, isomers of propylphenol, isomers of butylphenol.

According to a sixth embodiment, the present invention relates to a process according to any of the embodiments 1 to 5, wherein the diarylurethane of the general formula (3) is selected in a way that the corresponding aromatic hydroxy compounds Ar—OH and Ar'—OH have a standard boiling point lower than the diisocyanate OCN—R—NCO.

According to a seventh embodiment, the present invention relates to a process according to any of the embodiments 1 to 6, wherein the hydroxy compounds R'—OH and R"—OH in the transesterification are used in an amount that the combined number of OH groups from R'—OH and R"—OH is higher than that of the urethane groups in the reaction mixture.

According to a eighth embodiment, the present invention relates to a process according to any of the embodiments 1 to 7, wherein the hydroxy compounds R'—OH and R"—OH are aromatic hydroxy compounds.

According to a ninth embodiment, the present invention relates to a process according to any of the embodiments 1 to 7, wherein the hydroxy compounds R'—OH and R"—OH are fatty alcohols.

According to a tenth embodiment, the present invention relates to a process according to any of the embodiments 1 to 9, wherein a lewis acidic catalyst is used in the transesterification.

According to a eleventh embodiment, the present invention relates to a process according to any of the embodiments 1 to 9, wherein the cleavage reaction is a thermolytic cleavage that is carried out in a thin film evaporator.

According to a twelfth embodiment, the present invention relates to a process according to any of the embodiments 1 to 10, wherein a catalyst is used in the cleavage reaction.

According to a thirteenth embodiment, the present invention relates to a process according to any of the embodiments 1 to 12 for preparing an organic diisocyanate of the general formula (1)

OCN—R—NCO (1)

wherein
R represents a bivalent hydrocarbon radical which can be derived from 2,4-toluene diisocyanate, 2,6-toluene diisocyanate, hexamethylene diisocyanate, pentamethylene diisocyanate or isophoronediisocyanate by removing the two isocyanate groups, comprising the following steps:
(I) preparing a diurethane of the general formula (2),

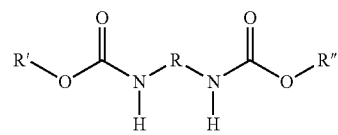

(2)

wherein
R is the same as in general formula (1),
R' represents a hydrocarbon-substituted or unsubstituted aryl radical selected from the group consisting of 6 to 20 carbon atoms and 5 to 33 hydrogen atoms that is bound to the urethane group of the diurethane of the general formula (2) via a carbon atom that is part of an aromatic ring system and
R" is the same as R',
from a diarylurethane of the general formula (3),

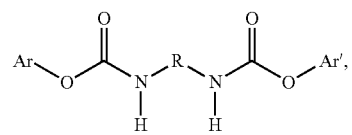

(3)

wherein
R is the same as in general formula (1) and
Ar represents a hydrocarbon-substituted or unsubstituted aryl radical selected from the group containing a total of 6 to 15 carbon atoms and having a lower molecular weight than the radical R' and
Ar' is the same as Ar
by transesterification reaction
(II) subjecting the diurethane of the general formula (2) to a cleavage reaction to form the aromatic hydroxy compounds R'—OH and R"—OH and the organic diisocyanate of the general formula (1),
(III) separating the diisocyanate of the general formula (1) from the aromatic hydroxy compounds R'—OH and R"—OH by distillation,
characterized in that
the aromatic hydroxy compounds R'—OH and R"—OH have a higher standard boiling point than the standard boiling point of the diisocyanate OCN—R—NCO, and
the aromatic hydroxy compounds Ar—OH and Ar'—OH, formally derived from Ar or Ar' respectively by adding a hydroxy group, has a lower standard boiling point than the standard boiling point of the diisocyanate OCN—R—NCO.

According to a fourteenth embodiment, the present invention relates to a process according to any of the embodiments 1 to 12 for preparing hexamethylene diisocyanate as diisocyanate of the general formula (1)

OCN—R—NCO (1)

comprising the following steps:

(I) preparing N,N'-hexanediyl-di(carbamic acid(4-cumylphenyl)ester) as diurethane of the general formula (2)

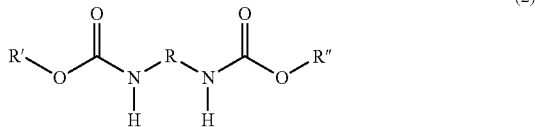

by a transesterification reaction of 1,6-hexamethylene-O,O'-diphenylurethane as diarylurethane of the general formula (3)

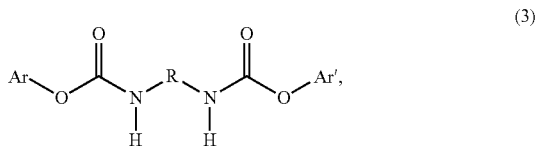

with p-cumylphenol.

(II) subjecting N,N'-hexanediyl-di(carbamic acid(4-cumylphenyl)ester) as diurethane of the general formula (2) to a thermal cleavage reaction to form p-cumylphenol and hexamethylene diisocyanate (HDI)

(III) separating the HDI from the p-cumylphenol by distillation.

The present invention will be explained in more detail below with reference to exemplary embodiments.

Example 1A (Comparative Example)

The comparative example 1 is the formation of N,N'-hexanediyl-di(carbamic acid(4-cumylphenyl)ester) according to the method described in example 14 (step 14-1) of EP 2 679 575 A1 on a technical scale.

A first raw material mixture A is prepared that contains 2.9 wt % of HDA, 4.6 wt % of urea and 92.5 wt % of p-cumylphenol. A second raw material mixture B is prepared that contains 7.5 wt % of urea and 92.5 wt % of p-cumylphenol. Mixture A is then introduced into a heated reaction column at a rate of 70 t/h and mixture B is introduced at a rate of 29.3 t/h. Accordingly, the total mass flows of the individual components into the reaction column are 2.0 t/h for HDA, 5.4 t/h for urea and 91.8 t/h for p-cumylphenol. The molar ratio of the compounds is about 25:5:1 (p-cumylphenol:urea:HDA).

The reaction is performed at 2 kPa and 215° C. with removal of ammonia from the reaction system. The desired N,N'-hexanediyl-di(carbamic acid(4-cumylphenyl)ester) is formed in good yield.

Example 1b (Thermal Cleavage)

The product of example 1a can be subjected to thermal cleavage which results in the formation of hexamethylenediisocyanate (HDI) and p-cumylphenol. A process for this thermal cleavage is described in example 14 (step 14-3) with reference to example 9 (step 9-3) of EP 2 679 575 A1. The gaseous cleavage products are introduced into a distillation column, where pure HDI is obtained as the distillate whereas p-cumylphenol is contained in the bottom product of the distillation.

Example 2a (Process According to the Invention, Step (I) According to the Present Invention)

In a first step, 1,6-hexamethylene-O,O'-diphenylurethane is prepared. The method is again based on the method from example 14 (step 14-1) to allow better comparison. Of course it is also possible to adapt the methods described in EP 0 320 235 A2. A first raw material mixture C is prepared that contains 6.8 wt % of HDA, 11.6 wt % of urea and 81.6 wt % of phenol. A second raw material mixture D is prepared that contains 11 wt % of urea and 89 wt % of phenol. Mixture C is then introduced into a heated reaction column at a rate of 30 t/h and mixture D is introduced at a rate of 18 t/h. Accordingly the total mass flows of the individual components into the reaction column are, 2.0 t/h for HDA, 5.4 t/h for urea and 40.5 t/h of phenol. The molar ratio of the compounds is about 25:5:1 (phenol:urea:HDA).

The reaction is performed at 2 kPa and 215° C. with removal of ammonia from the reaction system. The desired 1,6-hexamethylene-O,O'-diphenylurethane is formed in good yield.

Example 2B (Transesterification, Step (II) According to the Present Invention)

The product of example 2a can be subjected to a transesterification reaction, adapting methods known from the literature (see for example [0054-0061] of EP 2088 137 B1 or [0347-0370] of EP 2 679 575 A1). For that purpose, the content of 1,6-hexamethylene-O,O'-diphenylurethane in the product mixture from example 2a is determined before it is transferred to a column type transesterification reactor where it is converted with excess amount of p-cumylphenol. Phenol contained in the reaction mixture is removed from the reaction system via the vapor phase in order to drive the equilibrium reaction towards the desired product N,N'-hexanediyl-di(carbamic acid(4-cumylphenyl)ester).

Example 2C (Thermal Cleavage & Distillation, Steps (III) and (IV) According to the Present Invention)

The product of example 2b can be subjected to thermal cleavage which results in the formation of hexamethylenediisocyanate (HDI) and p-cumylphenol. A process for this thermal cleavage is described in example 14 (step 14-3) with reference to example 9 (step 9-3) of EP 2 679 575 A1. The gaseous cleavage products are introduced into a distillation column, where pure HDI is obtained as the distillate whereas p-cumylphenol is contained in the bottom product of the distillation.

DISCUSSION OF THE EXAMPLES

When comparing examples 1a and 2a, it can be seen that even though the same stoichiometric ratios of aromatic hydroxy compound:urea:diamine are used, the mass flow of the aromatic hydroxy compound is significantly reduced. The high stoichiometric excess of urea and aromatic hydroxy compound is required in order to suppress the formation of higher oligomers and/or polymers that would cause fouling inside the reaction system. Therefore, for converting 2.0 t/h of HDA, a total of 91.8 t/h of the p-cumylphenyl has to be fed to the reactor, some of which will be lost due to thermal decomposition to phenol and alpha-methylstyrene. Even though most of it can be recycled, the high mass flow renders the process uneconomical as the material has to be molten, heated, pumped, condensed etc. and it simply requires larger equipment to handle the large amounts. In comparison, the mass flow of phenol (40.5 t/h) is less than half while the stoichiometric ratios are kept constant.

The invention claimed is:

1. A process for preparing an organic diisocyanate of the general formula (1)

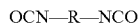  (1)

wherein
R represents a bivalent hydrocarbon radical containing 3 to 20 carbon atoms, the carbon atoms being arranged such that the two nitrogen atoms are separated from each other by at least 3 carbon atoms,
comprising the following steps:
(I) preparing a diurethane of the general formula (2),

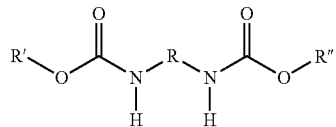  (2)

wherein
R is the same as in general formula (1),
R' and R" independently represent organic radicals consisting of 4 to 36 carbon atoms, 4 to 74 hydrogen atoms, 0 to 12 oxygen atoms that have the oxidation state −2, and 0 to 1 halogen atoms from a diarylurethane of the general formula (3),

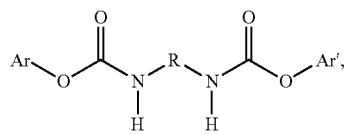  (3)

wherein
R is the same as in general formula (1),
Ar and Ar' independently represent a substituted or unsubstituted aryl or heteroaryl radical containing a total of 4 to 20 carbon atoms by transesterification reaction,
(II) subjecting the diurethane of the general formula (2) to a cleavage reaction to form the hydroxy compounds R'—OH and R"—OH and the organic diisocyanate of the general formula (1),
(III) separating the diisocyanate of the general formula (1) from the hydroxy compounds R'—OH and R"—OH by distillation,
wherein,
the hydroxy compounds R'—OH and R"—OH have higher standard boiling points than the standard boiling point of the diisocyanate OCN—R—NCO, and
the sum of the molecular weights of the radicals Ar and Ar' is lower than the sum of the molecular weights of the radicals R' and R".

2. The process according to claim 1, wherein the diarylurethane of the formula (3) is prepared from organic diamines, carbonic acid derivatives and aromatic hydroxy compounds.

3. The process according to claim 2, wherein the organic diamine is selected from the group consisting of 2,4-toluylendiamine, 2,6-toluylendiamine, 2,2'-diaminodiphenylmethane, 2,4'-diaminodiphenylmethane, 4,4'-diaminodiphenylmethane, 1,5-naphthalenediamine, 1,3-diaminobenzene, 1,4-diaminobenzene, m-xylylenediamine, p-xylylendiamine, 1,4-butanediamine, neopentanediamine, 1,5-pentanediamine, 1,5-diamino-2-methylpentane, 2-butyl-2-ethyl-1,5-pentanediamine, 1,6-hexanediamine, 2,5-diamino-2,5-dimethylhexane, 1-amino-3,3,5-trimethyl-5-aminomethyl-cyclohexane, 1,4-cyclohexanediamine, 2,4-hexahydrotoluenediamine, 2,6-hexahydrotoluenediamine, isomers of hexahydroxylylendiamine, isomers of bis-(aminomethyl)norbornane, and mixtures of the aforementioned.

4. The process according to claim 2, wherein the carbonic acid derivative is urea, diarylcarbamate or dialkylcarbonate.

5. The process according to claim 2, wherein the aromatic hydroxy compound is selected from the group consisting of phenol, o-cresol, m-cresol, p-cresol, 2,6-xylenol, 2,5-xylenol, 2,4-xylenol, 2,3-xylenol, 3,4-xylenol, 3,5-xylenol, mesitol, o-ethylphenol, m-ethylphenol, p-ethylphenol, isomers of propylphenol, and isomers of butylphenol.

6. The process according to claim 1, wherein the diarylurethane of the general formula (3) is selected such that the corresponding aromatic hydroxy compounds Ar—OH and Ar'—OH have a standard boiling point lower than the diisocyanate OCN—R—NCO.

7. The process according to claim 1, wherein the hydroxy compounds R'—OH and R"—OH in the transesterification are used in an amount that the combined number of OH groups from R'—OH and R"—OH is higher than that of the urethane groups in the reaction mixture.

8. The process according to claim 1, wherein the hydroxy compounds R'—OH and R"—OH are aromatic hydroxy compounds.

9. The process according to claim 1, wherein the hydroxy compounds R'—OH and R"—OH are selected from the group consisting of lauryl, stearyl, cetyl and oleyl alcohol.

10. The process according to claim 1, wherein a Lewis acidic catalyst is used in the transesterification.

11. The process according to claim 1, wherein the cleavage reaction is a thermolytic cleavage carried out in a thin film evaporator.

12. The process according to claim 1, wherein a catalyst is used in the cleavage reaction.

13. A process according to claim 1 for preparing an organic diisocyanate of the general formula (1)

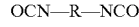  (1)

wherein
R represents a bivalent hydrocarbon radical derived from 2,4-toluene diisocyanate, 2,6-toluene diisocyanate, hexamethylene diisocyanate, pentamethylene diisocyanate or isophoronediisocyanate by removing the two isocyanate groups, comprising the following steps:
(I) preparing a diurethane of the general formula (2),

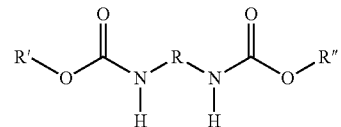  (2)

wherein
R is the same as in general formula (1),

R' represents a hydrocarbon-substituted or unsubstituted aryl radical consisting of 6 to 20 carbon atoms and 5 to 33 hydrogen atoms that is bound to the urethane group of the diurethane of the general formula (2) via a carbon atom that is part of an aromatic ring system and R" is the same as R', from a diarylurethane of the general formula (3),

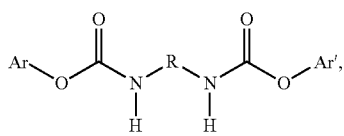

(3)

wherein
R is the same as in general formula (1) and
Ar represents a hydrocarbon-substituted or unsubstituted aryl radical containing a total of 6 to 15 carbon atoms and having a lower molecular weight than the radical R' and
Ar' is the same as Ar by transesterification reaction (II) subjecting the diurethane of the general formula (2) to a cleavage reaction to form the aromatic hydroxy compounds R'—OH and R"—OH and the organic diisocyanate of the general formula (1), (III) separating the diisocyanate of the general formula (1) from the aromatic hydroxy compounds R'—OH and R"—OH by distillation, wherein
the aromatic hydroxy compounds R'—OH and R"—OH have a higher standard boiling point than the standard boiling point of the diisocyanate OCN—R—NCO, and
the aromatic hydroxy compounds Ar—OH and Ar'—OH, formally derived from Ar or Ar' respectively by adding a hydroxy group, has a lower standard boiling point than the standard boiling point of the diisocyanate OCN—R—NCO.

14. A process according to claim 1 for preparing hexamethylene diisocyanate as diisocyanate of the general formula (1)

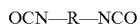   (1)

comprising the following steps:
(I) preparing N,N'-hexanediyl-di(carbamic acid(4-cumylphenyl)ester) as diurethane of the general formula (2)

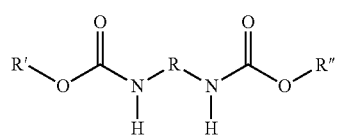

(2)

by a transesterification reaction of 1,6-hexamethylene-O,O'-diphenylurethane as diarylurethane of the general formula (3)

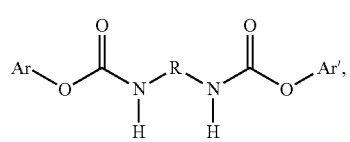

(3)

with p-cumylphenol,
(II) subjecting N,N'-hexanediyl-di(carbamic acid(4-cumylphenyl)ester) as diurethane of the general formula (2) to a thermal cleavage reaction to form p-cumylphenol and hexamethylene diisocyanate (HDI)
(III) separating the HDI from the p-cumylphenol by distillation.

* * * * *